(12) United States Patent
Marshall et al.

(10) Patent No.: US 12,263,077 B2
(45) Date of Patent: Apr. 1, 2025

(54) VASCULAR GRAFTS AND METHOD FOR PRESERVING PATENCY OF THE SAME

(71) Applicant: Healionics Corporation, Seattle, WA (US)

(72) Inventors: Andrew J. Marshall, Seattle, WA (US); Max Maginness, Seattle, WA (US); Adrienne Oda, Seattle, WA (US); Brandt Scanlan, Seattle, WA (US)

(73) Assignee: Healionics Corporation, Seattle, WA (US)

( * ) Notice: Subject to any disclaimer, the term of this patent is extended or adjusted under 35 U.S.C. 154(b) by 401 days.

(21) Appl. No.: 17/457,246

(22) Filed: Dec. 1, 2021

(65) Prior Publication Data

US 2022/0087811 A1 Mar. 24, 2022

Related U.S. Application Data

(60) Division of application No. 16/457,530, filed on Jun. 28, 2019, now abandoned, which is a continuation of application No. 14/627,871, filed on Feb. 20, 2015, now abandoned.

(60) Provisional application No. 61/984,537, filed on Apr. 25, 2014, provisional application No. 61/943,178, filed on Feb. 21, 2014.

(51) Int. Cl.
*A61F 2/06* (2013.01)
*A61F 2/00* (2006.01)
*A61L 31/04* (2006.01)
*A61L 31/14* (2006.01)

(52) U.S. Cl.
CPC ............. *A61F 2/06* (2013.01); *A61F 2/0077* (2013.01); *A61L 31/04* (2013.01); *A61L 31/146* (2013.01); *A61F 2002/0081* (2013.01); *A61F 2210/0076* (2013.01)

(58) Field of Classification Search
CPC .. A61F 2/06; A61F 2/07; A61F 2/0077; A61F 2002/0081; A61F 2210/0076; A61L 31/04; A61L 31/146
See application file for complete search history.

(56) References Cited

U.S. PATENT DOCUMENTS

| | | | | |
|---|---|---|---|---|
| 8,318,193 B2* | 11/2012 | Ratner | ............... | A61F 2/0077 424/424 |
| 8,372,423 B2* | 2/2013 | Marshall | ............... | A61P 31/00 424/423 |
| 2003/0017775 A1* | 1/2003 | Sowinski | ............... | A61F 2/06 428/36.1 |

* cited by examiner

*Primary Examiner* — Christopher D. Prone
(74) *Attorney, Agent, or Firm* — Seed IP Law Group LLP

(57) ABSTRACT

This disclosure provides prosthetic arteriovenous grafts having a blood-contacting layer; an intermediate layer; and a tissue-interface layer formed of a microporous biomaterial with a textured microporous surface, the prosthetic arteriovenous grafts providing vascular access for hemodialysis and being capable of reducing perigraft fibrotic capsular formation, and a method of maintaining the patency of the prosthetic arteriovenous grafts.

20 Claims, 13 Drawing Sheets

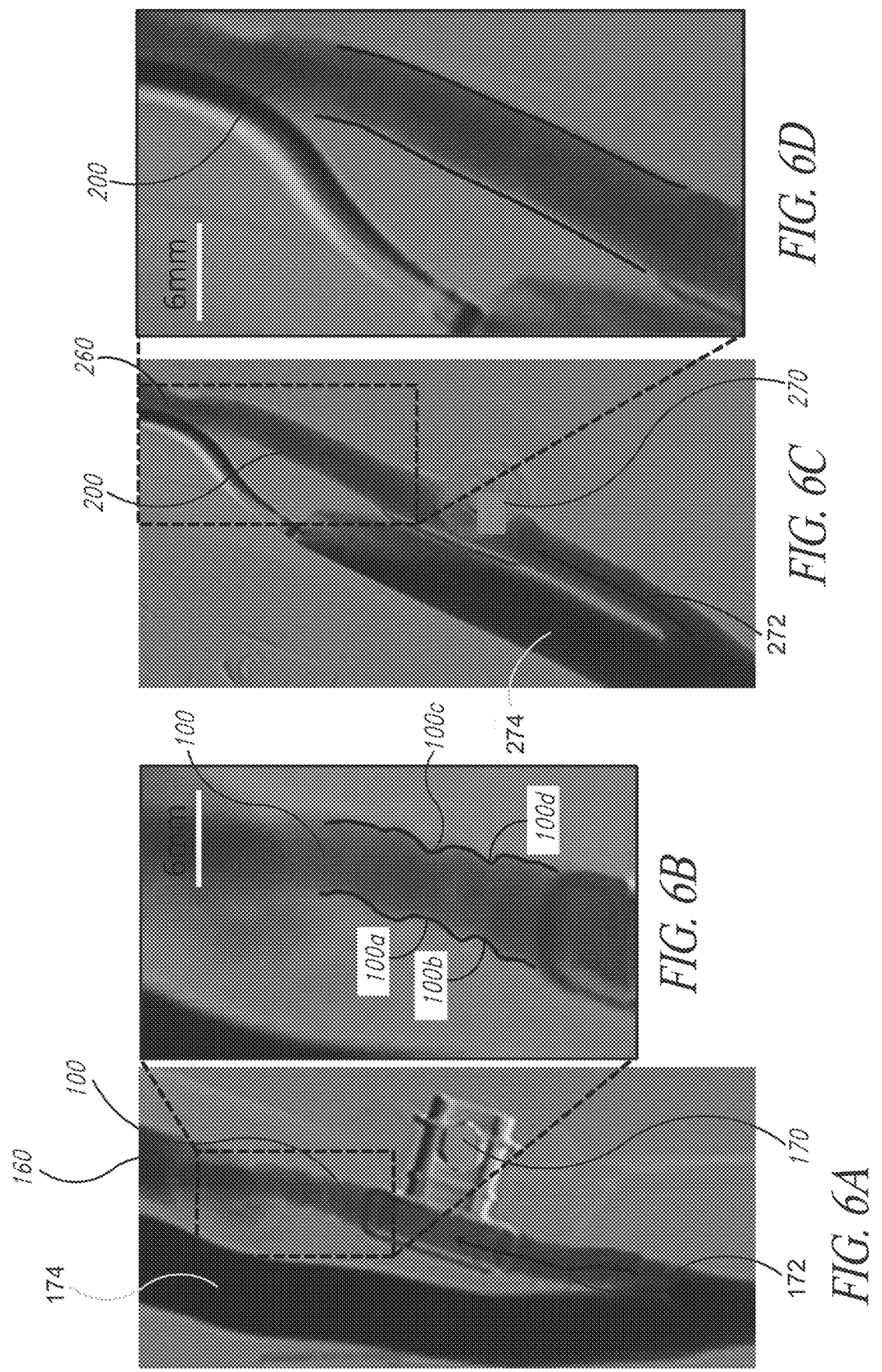

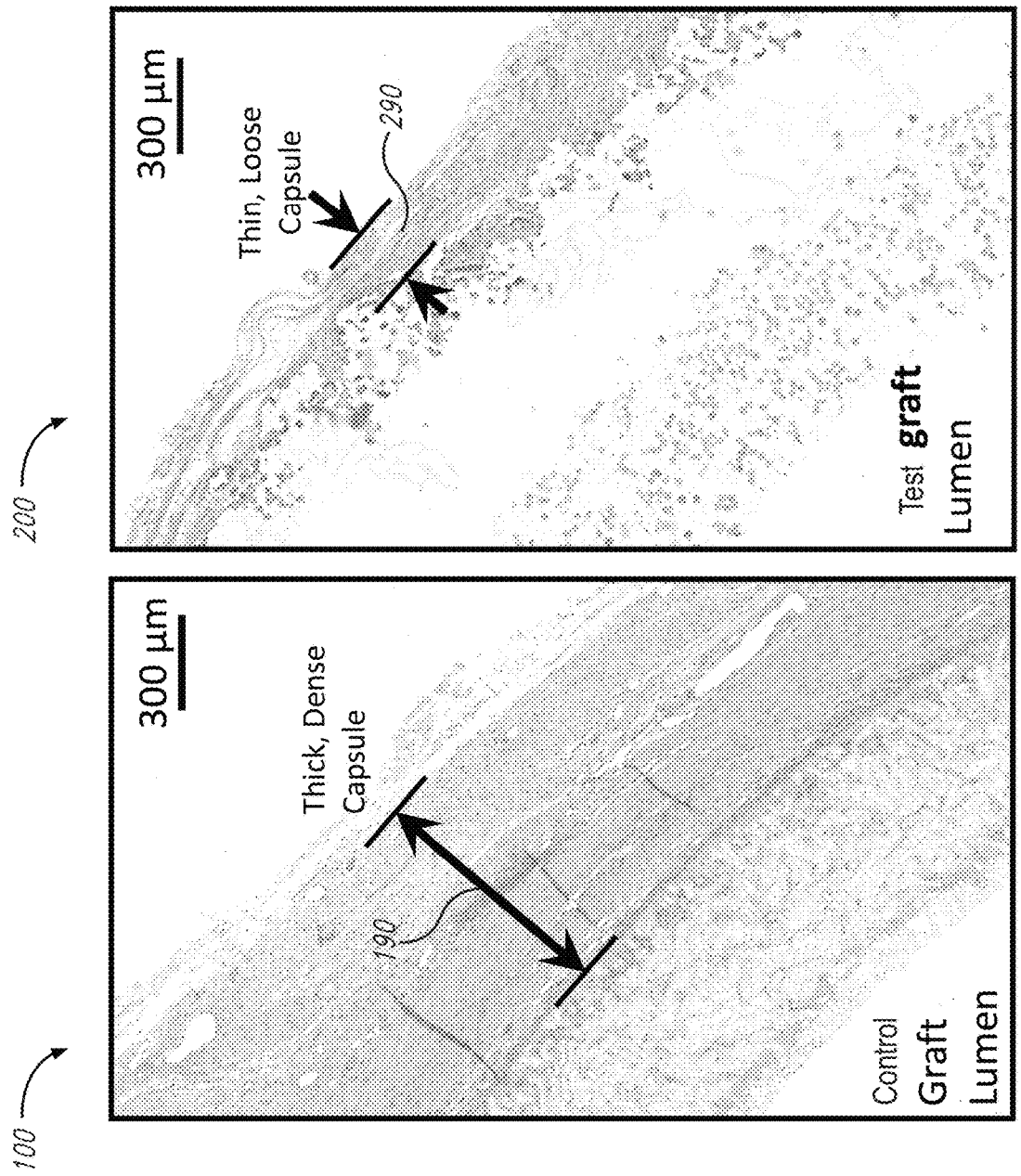

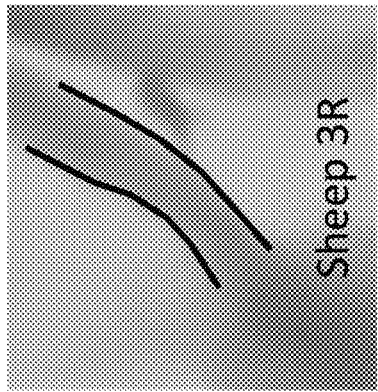
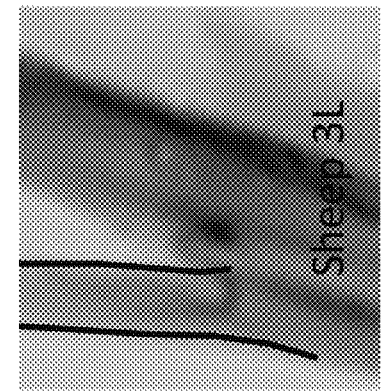
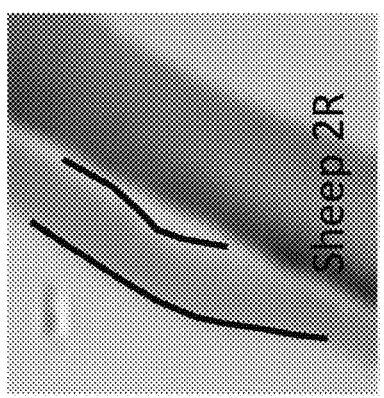
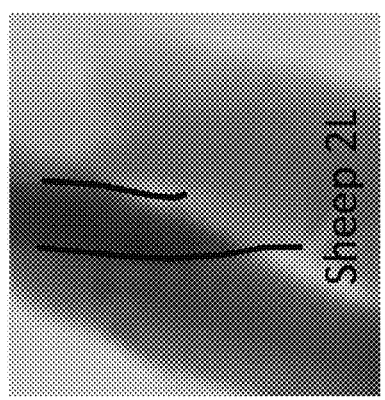
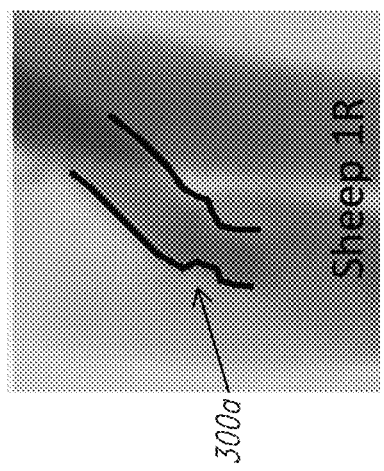
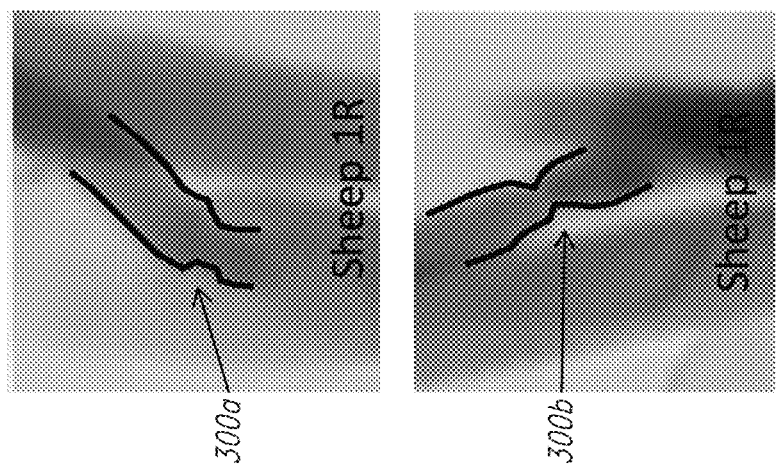
FIG. 12A
FIG. 12B

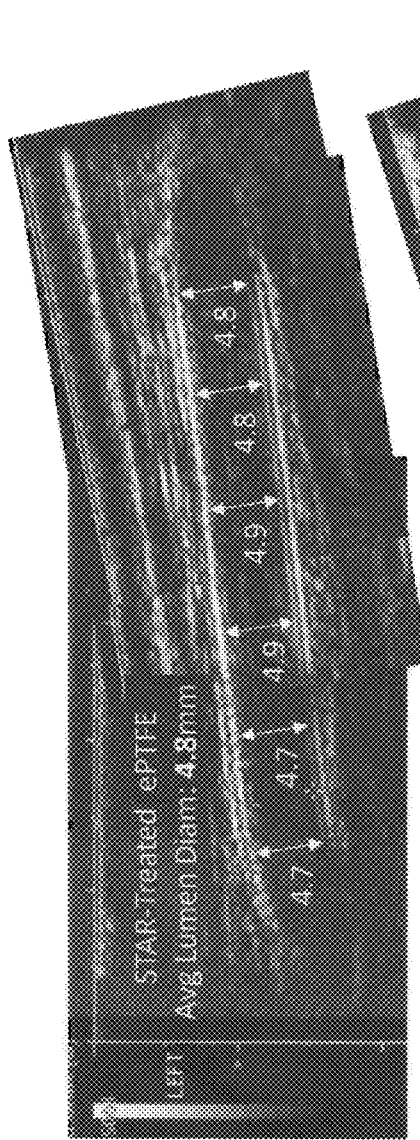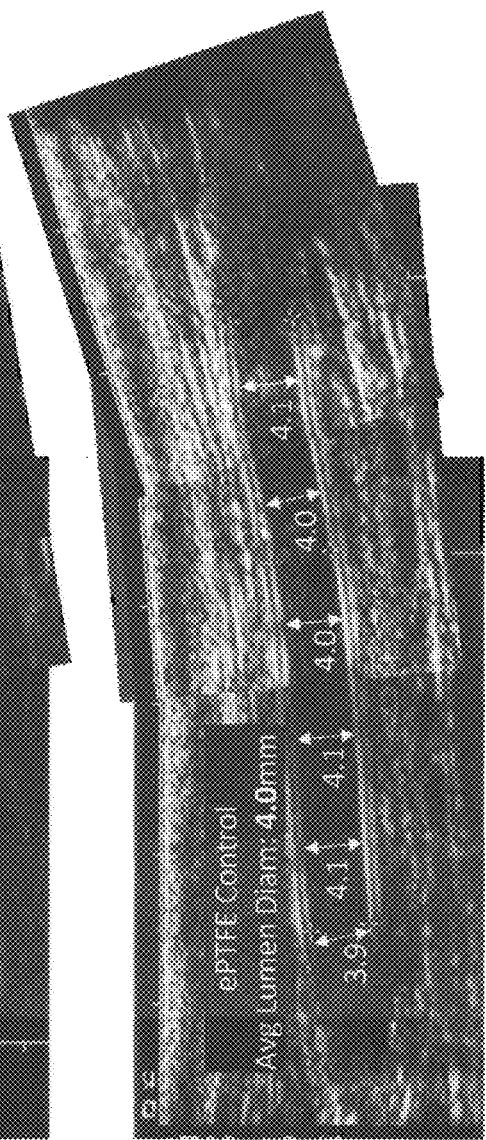
FIG. 17A
FIG. 17B

VASCULAR GRAFTS AND METHOD FOR PRESERVING PATENCY OF THE SAME

CROSS-REFERENCES TO RELATED APPLICATIONS

This application is a divisional of U.S. application Ser. No. 16/457,530, filed Jun. 28, 2019, which is a continuation of U.S. application Ser. No. 14/627,871, filed Feb. 20, 2015 (now abandoned), which claims the benefit under 35 U.S.C. § 119 (e) of U.S. Provisional Patent Application Nos. 61/943,178, filed Feb. 21, 2014, and 61/984,537, filed Apr. 25, 2014, which applications are incorporated herein by reference in their entireties.

STATEMENT OF GOVERNMENT INTEREST

This invention was made with government support under DK103512, HL126256, GM093697, and DK118380 awarded by the National Institutes of Health. The government has certain rights in the invention.

BACKGROUND

Technical Field

This invention relates to vascular grafts, such as artificial blood vessels.

Description of the Related Art

Prosthetic vascular grafts are artificial tubular blood conduits or patches. They are commonly used to replace or repair diseased segments of natural arteries or veins. They are also routinely used as arteriovenous shunts to present a suitable vascular access site for dialysis treatment.

To form an anastomosis with a native blood vessel, a vascular graft is directly connected (e.g., by suturing) at the ends of the graft to the cut edges of a native vessel ("end-to-end") or to the side of the native vessel ("end-to-side").

The most common vascular graft materials include porous expanded polytetrafluoroethylene (ePTFE) and porous polyethylene terephthalate (Dacron®). They can also be made from porous elastomeric materials such as silicone or polyurethane.

FIG. 1 shows a conventional elastomeric polyurethane-based vascular graft in a Tri-Layer Thoralon® Design. More specifically, the vascular graft (100) comprises a microporous inner layer (110), a solid intermediate layer (120) and a microporous outer layer (130). The microporous inner layer (110) is the blood-contacting layer when in use. Its microporous structure is generally rich with surface modifying additives (SMA) to enhance blood-device compatibility and to minimize platelet adhesion. The solid intermediate layer (120) prevents any communicating pathway between the inner and outer layers and gives the graft its strength, flexibility and self-sealing properties. The microporous outer layer (130) is designed to enhance graft anchoring by promoting fibrotic tissue ingrowth. The microporous outer layer (130) is embedded with thin monofilament polyester fibers (134) to provide reinforcement and kink resistance.

The most common complication with vascular grafts is stenosis, i.e., a narrowing or stricture at the outflow anastomosis, which leads to thrombosis and occlusion of the graft. The occlusive failure of the grafts can be especially severe for replacements of small caliber vessels (less than 6 mm internal diameter), limiting the use of prosthetic grafts in these cases. Stenosis also presents a major medical problem in dialysis care. For the large fraction of hemodialysis patients who cannot sustain an access site from modifying natural vessels into an arteriovenous fistula, prosthetic arteriovenous graft is the safest option for long-term vascular access. However, occlusive failure could limit the average lifespan of a dialysis graft to less than two years.

Thus, there remains a need to address the occlusive failure from thrombosis at the outflow anastomosis in vascular grafts.

BRIEF SUMMARY

Disclosed herein are vascular grafts capable of maintaining long-term patency and methods for maintain graft patency by using the same.

One embodiment provides a vascular graft comprising: a blood-contacting layer formed of a first microporous biomaterial; a nonporous intermediate layer; and a tissue-interface layer having a textured microporous surface that contacts host tissue when implanted, the tissue-interface layer being formed of a second microporous biomaterial, wherein the textured microporous surface is capable of reducing fibrotic capsular formation.

Another embodiment provides a method of maintaining patency in the vascular graft described above, and comprises: pre-hydrating the vascular graft to remove any air in the first microporous biomaterial; and implanting the vascular graft by directly connecting the vascular graft to a native blood vessel.

BRIEF DESCRIPTION OF THE SEVERAL VIEWS OF THE DRAWINGS

FIGS. 6A-6D are angiography images of blood flow paths 2 months after implantation for a conventional ePTFE shunt versus a vascular graft according to an embodiment of the present disclosure.

FIGS. 9A and 9B show the exterior capsule tissue morphology for a conventional ePTFE graft and a vascular graft according to an embodiment of the present disclosure, respectively.

FIGS. 12A and 12B are fluoroscopic angiography images of the venous anastomosis region for conventional ePTFE grafts and vascular grafts according to an embodiment of the present disclosure, respectively.

FIGS. 17A and 17B are Doppler ultrasound images of longitudinal cross sections of a conventional ePTFE graft and a contralaterally implanted graft according to an embodiment of the present disclosure, respectively.

DETAILED DESCRIPTION

Figure 1:
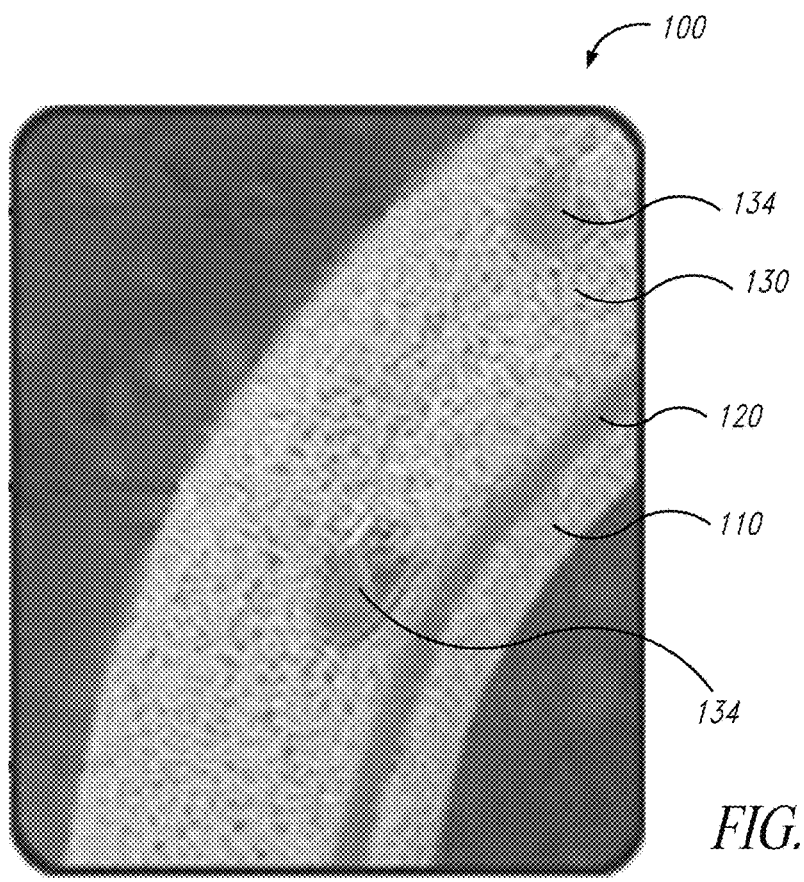
FIG. 1 is a cross section of a conventional vascular graft.

Conventional vascular grafts generally have certain surface features for better anchorage in the tissue. For instance, a microporous outer layer is typically designed to promote fibrous tissue ingrowth with the micropores. See FIG. 1. As a result, the graft is anchored as it becomes partially or completely encapsulated in fibrous tissue.

As discussed herein, it has been unexpectedly discovered by the present inventors that the fibrotic encapsulation, while a useful feature for graft anchorage, contributes to graft stenosis, which can progress to occlusive failure of the graft. Thus, disclosed herein are vascular grafts that reduce fibrotic encapsulation. Owing to surface features that include tightly controlled surface topography and microporosities, the vascular grafts of the various embodiments are capable of minimizing stenosis, thereby enhancing the lifetime of the grafts. Also disclosed are methods of preserving long-term patency of a vascular graft.

Stenosis and Capsular Contraction

Stenosis is known to occur due to neointimal hyperplasia and thrombotic deposition, which are mediated by the flow characteristics of the blood within the lumen. In particular, reduced flow, which correlates to lowered Wall Shear Stresses (WSS), favors the development of intimal hyperplasia and thrombotic deposition. This correlation between flow and hyperplasia creates a feedback loop of progressively pathologic WSS. Once stenosis begins to occur due to hyperplasia, the stenosis itself constricts the blood flow, which causes even lower WSS, thereby accelerating the rate of stenosis.

Conventional approaches to minimizing or managing stenosis include promoting more favorable WSS conditions, e.g., by improving hemodynamics or reducing compliance mismatch between the graft and the native vessels. One example for reducing the effects of compliance mismatch is to use interrupted sutures at the anastomosis, which allows each suture to move independently. Other known techniques that seek to widen the venous anastomosis of dialysis grafts, thereby diffusing the flow and providing more favorable hemodynamics, have also been shown to be beneficial. However, none of the conventional approaches have achieved wide acceptance in a clinical setting.

As discussed herein, it has been unexpectedly discovered that capsular contraction can be a primary contributor to graft stenosis. When capsular contraction occurs, the constricting force from collagen lattice contraction radially compresses the graft. Because a vascular graft is typically made from flexible porous polymers, the radial compression narrows the lumen. Narrower lumen leads to a drop in flow rate, which is associated with reduced WSS. The reduced WSS in turn causes upregulation of neointimal hyperplasia and thrombotic deposition, compounding the effect by promoting further stenosis.

Thus, according to various embodiments, vascular grafts capable of suppressing fibrotic encapsulation can effectively minimize or alleviate stenosis that otherwise would have developed due to capsular contraction during the first months of implant. In particular, it has been discovered that when the fibrotic encapsulation is suppressed, the vascular graft retains the ability to expand radially. As neointimal hyperplasia initially develops at the outflow end of the graft and causes mild stenosis, pressure in the lumen increases. In response, the graft expands radially, thus reducing resistance to flow and compensating for the stenosis. Under certain conditions, the enhanced radial compliance can create a net increase in the graft flow in response to the hyperplasia at the outflow, which creates a self-stabilizing effect.

Vascular Graft

Various embodiments are directed to vascular grafts configured to suppress fibrotic encapsulation.

Figure 2:
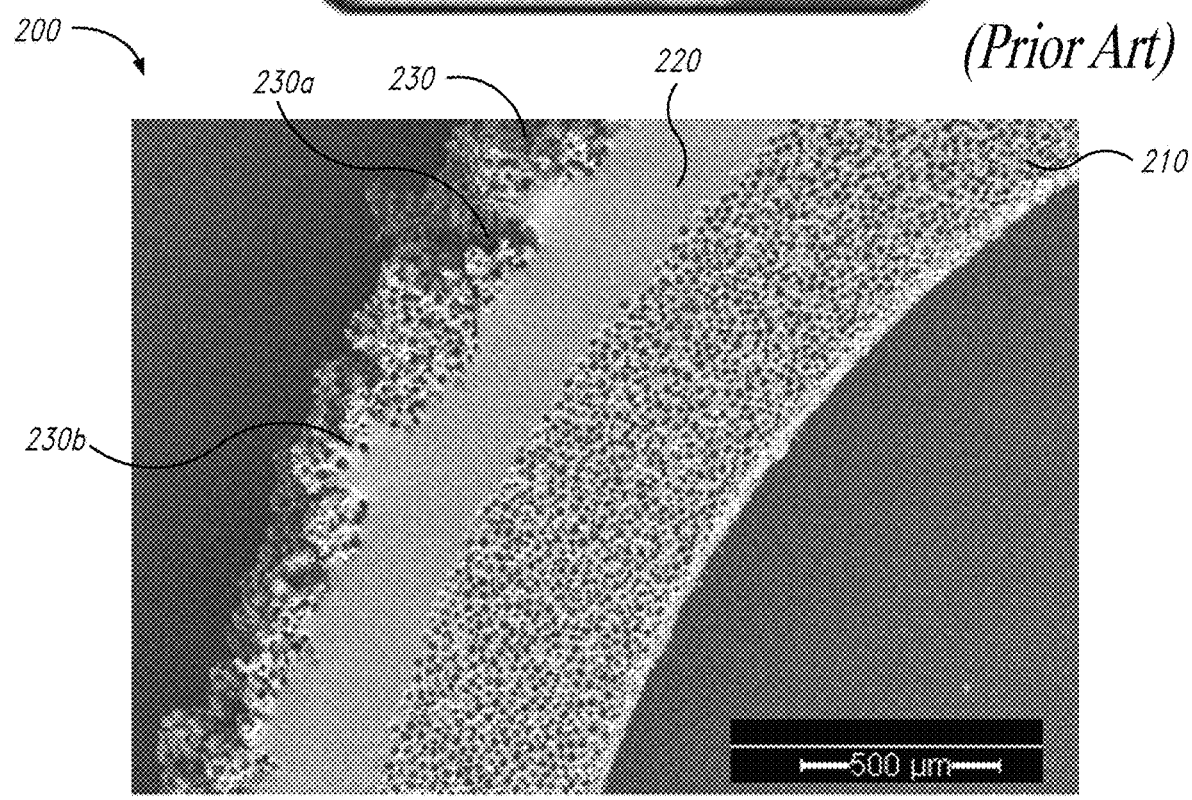
FIG. 2 is a cross section of a vascular graft made entirely of elastomeric silicone according to an embodiment of the present disclosure.

FIG. 2 shows a vascular graft according to an embodiment. More specifically, the vascular graft (200) comprises: a blood-contacting layer (210) formed of a first microporous biomaterial; a nonporous intermediate layer (220); and a tissue-interface layer (230) having a textured microporous surface that contacts host tissue when implanted, the tissue-interface layer being formed of a second microporous biomaterial, wherein the textured microporous surface is capable of reducing fibrotic capsular formation. More specifically, the textured microporous surface has both microporosity and macrotextures that have depressions (230a) and protrusions (230b). As discussed in further detail below, the textured microporous surface allows for vascularized tissue ingrowth (as opposed to fibrotic tissue ingrowth) in the micropores and as such, reduces fibrotic encapsulation.

In the embodiment shown in FIG. 2, the entire graft is composed of elastomeric materials, such as silicone or polyurethane-based co-polymers. Elastomeric mechanical properties are particularly advantageous when used in combination with the capsule-suppressing exterior surface geometry of the present invention.

Figure 3:
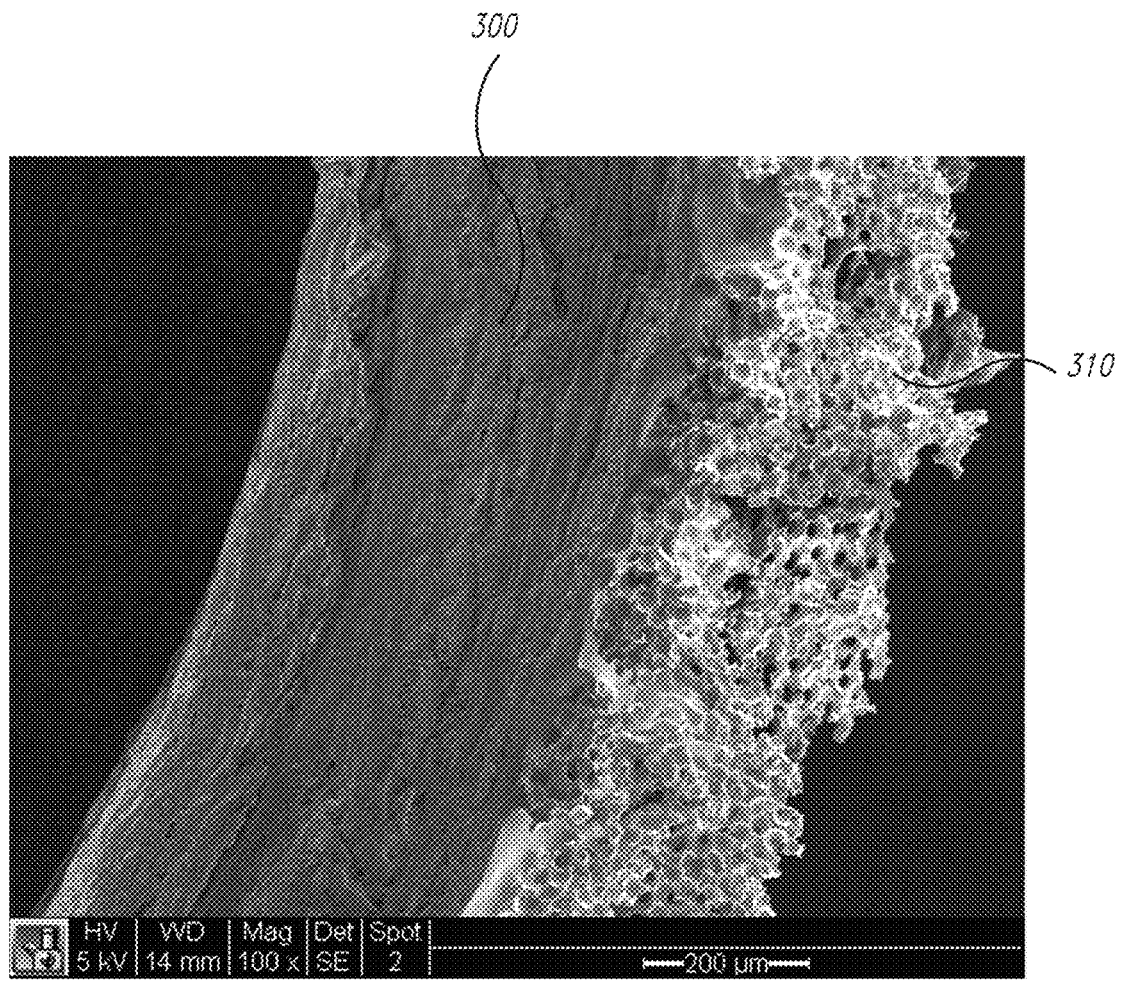
FIG. 3 shows a cross section of a vascular graft according to another embodiment, in which a conventional ePTFE graft is modified with microporous and macrotextured surface geometry.
Figure 4:
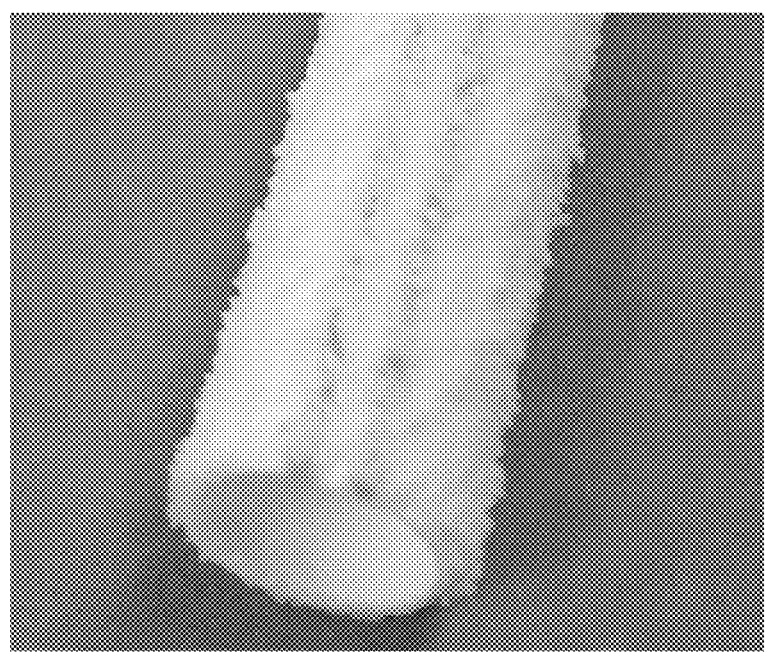
FIG. 4 shows another view of the vascular graft of FIG. 3.

Another embodiment is shown in FIG. 3, in which a conventional graft (300), such as an ePTFE graft, is surface-treated to provide a tissue-interface layer (310). In certain embodiments, the tissue-interface layer comprises granules of various sizes made of the second microporous material. The sizes of the granules define macrotextures, similar to those of FIG. 2. FIG. 4 is another view of such a vascular graft coated with a textured microporous surface layer.

As used herein, "vascular graft" or "graft" refers to a flexible tubular structure or a patch that can be coupled directly to native blood vessels.

"Fibrotic encapsulation" or "fibrotic capsular formation" refers to the formation of a dense, fibrous, largely avascular capsule that partially or completely surrounds an implant such as a vascular graft. Implantation of a foreign object naturally induces an inflammatory reaction of the body, also referred to as foreign body response (FBR). In the first hours of the FBR, host macrophages are attracted to the surface of the implant. The macrophages arrive in sufficient numbers to spread over all surfaces of the implant that interface with the host tissue. When the surface of the implant is smooth and impermeable to cells, these macrophages trigger a cascade of cytokines and chemokines that recruit fibroblasts and other extracellular matrix-building cells to the tissue adjacent to the implant. The degree of fibrotic encapsulation can be measured by the thickness of the dense fibrotic capsules surrounding the implant.

As used herein, "reducing" fibrotic encapsulation is relative to fibrotic encapsulation that would have occurred in the absence of the textured microporous surface. In certain embodiments, "reducing" fibrotic encapsulation refers to at least 20%, or at least 30%, or at least 40%, or at least 50%, or at least 60%, or at least 70%, or at least 80% of reduction over a period of 8 weeks or 12 weeks of implantation, as compared to the fibrotic encapsulation that would have occurred in an otherwise similarly constructed vascular graft but without the textured microporous surface.

"Microporous biomaterial" is a biocompatible material that may comprise an array of spherical or substantially spherical pores that are substantially connected. As used herein, "substantially connected" means that essentially every pore is connected to at least two, and preferably to at least four other pores. Typically, the mean pore diameter can be between 10 and 100 micrometers. The preferred pore diameter is between 20 and 40 micrometers, between 30 and 40 micrometers, between 25 and 35 micrometers, between 20 and 30 micrometers, or between 25 and 30 micrometers. Preferably, according to certain embodiments, the majority of the pores will be of such a preferred pore size. At these dimensions, the geometries of the pores may, according to non-limiting theory, constrain the invading macrophage cells and prevent them from spreading or aggregating into giant cells. The pore geometry thus may provide spatial cues that trigger the macrophages to secrete anti-fibrotic and pro-angiogenic factors.

The mean diameter of the connection between the pores (i.e., throat or interpore opening) may, in certain preferred embodiments, be between 5 and 50 micrometers. The preferred diameter of the pore connections is between 8 and 25 micrometers, more preferably between 10 and 20 micrometers. Preferably, the majority of the pore connections will be of the preferred size. A macrophage cell diameter is typically about 10 to 15 micrometers in size, so the pore connections should be large enough to accommodate facile cell migration though the scaffold. Also, vascular endothelial capillaries are typically about 10 micrometers in diameter, so the scaffold should have pore connections large enough to permit ingrowth of a capillary network to support and nourish cells inside the scaffold.

A microporous material that has continuously interconnected pores throughout the entire material is also called an "open pore" or "open cell" structure.

The first microporous biomaterial of the blood-contacting layer and the second microporous material of the tissue-interface layer may be the same or different. For example, they can be made of different materials, e.g., ePTFE for the blood contacting layer and silicone rubber for the tissue-interface layer. Furthermore, the first microporous material and the second microporous material are considered different even if they are of the same material (e.g., silicone rubber) but have different degrees of microporosity (pore sizes or interpore openings).

The components of the vascular grafts according to various embodiments are described in further detail below.

1. Blood-Contacting Layer

The blood-contacting layer is generally the innermost layer that defines the lumen of the graft. Because it contacts the blood, the microporosity of this layer is selected to minimize platelet adhesion. In certain embodiments, the blood-contacting layer is an open-pore microporous biomaterial with generally uniform pore diameter, where the pore diameter is larger than 20 microns and smaller than 50 microns, and wherein the diameter of substantially all interpore openings (e.g., more than 90%) between neighboring pores are larger than 5 microns and smaller than 30 microns.

In various embodiments, the biomaterial is a hydrogel, silicone rubber, expanded fluoropolymer, or a polymer.

In some embodiments, the inner blood contacting layer is composed of microporous sphere-templated biomaterial (STAR) as described in U.S. Pat. No. 7,792,628 (incorporated herein by reference in its entirety), which allows capillary ingrowth and has pore geometry suited for low thrombogenicity. This also improves infection resistance and resistance to bacterial biofilms by allowing immune cell access into every pore.

2. Tissue-Interface Layer

The tissue-interface layer is the outermost layer of the vascular graft that directly contacts the host tissue when implanted. The degree of microporosity of the tissue-interface layer is selected to minimize foreign body response and fibrotic encapsulation. In certain embodiments, the outer layer is a biomaterial that has interconnected pores that are larger than 20 microns and smaller than 200 microns, and where the connections between neighboring pores (i.e., interpore openings) are larger than 5 microns and smaller than 50 microns.

In various embodiments, the biomaterial is a hydrogel, silicone rubber, expanded fluoropolymer, or a polymer. Microporous biomaterials can be prepared according to methods disclosed in U.S. Pat. Nos. 7,972,628 and 8,318, 193, which are incorporated herein by reference in its entirety. Other suitable microporous biomaterials include porous polyurethane-based co-polymers or porous silicones as described in US20140005783 A1, US20140005784 A1, US20130209661 A1, US20130295379 A1, and U.S. Pat. No. 8,487,012 B2. Macrotextured microporous ePTFE, disclosed in U.S. Pat. No. 5,466,509 A, is also suitable.

The outer layer has a textured microporous surface, which refers to a bio-interface between the host tissue and the graft. The textured microporous surface, also referred to as "macrotextured," has surface topography that can contribute to reducing fibrotic capsule formation. In certain embodiments, the surface topography includes peaks and valleys of specific dimensions. More specially, a peak represents a projection or protrusion in the surface topography, whereas a valley represents a depression in the surface topography and is a space defined by two or more adjacent peaks. The height of a given peak is typically measured relative to the floor of the adjacent valley. In certain embodiments, the height of a peak is greater than 200 microns and less than 1000 microns.

An exemplary exterior surface geometry for reducing the foreign body response is the microporous and macrotextured geometry disclosed in U.S. Pat. Nos. 8,372,423 and 8,647, 393, in the name of Healionics Corporation, which patents are incorporated herein by references in their entireties. This surface geometry is optimized to promote a minimally-fibrotic densely vascularized ingrowth into the microporous structure, and also promotes a thinner, looser, less-aligned, more vascularized exterior tissue capsule. This surface geometry is particularly well-suited for covering a vascular graft because it also provides protection against bacterial colonization and infection, which is the second most common complication for vascular grafts.

Other materials shown to substantially reduce foreign body encapsulation, such as porous polyurethane-based copolymers or porous silicones as described in US20140005783 A1, US20140005784 A1, US20130209661 A1, US20130295379 A1, and U.S. Pat. No. 8,487,012 B2 could also be used for this purpose. Macrotextured microporous ePTFE, such as U.S. Pat. No. 5,466,509 A, for example, could also potentially be adapted for this purpose.

3. Intermediate Layer

The intermediate layer bonds the blood-contacting layer and the tissue-interface layer together. The intermediate layer thus could be an adhesive layer. In other embodiments, the intermediate layer is impermeable to blood and serum, thereby preventing leakage. This may confer the additional advantage of blocking cytokines from outside the graft to reach the lumen, as these cytokines could potentially promote neointimal hyperplasia. The layer can also be used to add toughness or suture retention strength.

Having a fully or partially impermeable layer has the added advantage of allowing the graft to be implanted in a prehydrated state by which the air in the pores (particularly those on the inner layer) has been fully displaced before implantation. The removal of air in the pores confers improved initial thromboresistance and improves infection resistance.

In other embodiments, the graft may have fenestrations in the impermeable layer to permit tissue ingrowth and angiogenesis from the adventitial surface.

In some embodiments, the intermediate layer may be non-porous but otherwise the same biomaterial as that of the blood-contacting layer or the tissue-interface layer. For example, in the vascular graft shown in FIG. 2, the entire graft is made of elastomeric silicone, in which the intermediate layer is non-porous. In other embodiments, the intermediate layer is an adhesive layer. For example, in the vascular graft shown in FIG. 3, a conventional ePTFE graft can be first coated with a biocompatible adhesive, thus forming the intermediate layer, followed by a coating of granules of a second microporous material to provide the textured microporous surface of the tissue-interface layer.

In some embodiments, the graft may be composed fully or partially of bioresorbable materials.

In some embodiments, the graft may comprise hydrogel.

In some embodiments, the graft may comprise gels or polymers made from natural proteins.

In some embodiments, the graft may comprise synthetic materials.

In some embodiments, the graft may have radial reinforcement features for kink resistance.

In some embodiments, the graft may have built-in prestresses (with the inner layer in axial tension, and the outer layer in axial compression) to improve kink resistance while preserving radial compliance.

In some embodiments, the microporous material can further be treated with agents, additives, or coatings for reducing thrombogenicity, resisting fibrotic encapsulation, resisting infection, or reducing hydrophobicity.

Maintaining Patency of Implanted Vascular Grafts

It has been unexpectedly discovered that a tissue interface surface capable of enabling radial expansion of the graft wall can encourage a compensatory and potentially self-stabilizing flow behavior in prosthetic grafts, which in turn contributes to maintaining patency of the graft. In particular, neointimal hyperplasia (known to be the primary cause of graft occlusion) was nearly completely suppressed by the presence of the textured microporous surface at the exterior of the graft that interfaces with the host tissue. In some cases, the compensatory flow effect occurs because the preserved radial compliance allows a change in the collapsibility of the graft. An increase in pressure within the graft causes an increase in the average hydraulic diameter because high-frequency hydraulic diameter fluctuations due to turbulence are attenuated. In this case, the compensatory flow effect depends on wall compliance, but does not require elastomeric wall properties.

In addition, patency can be improved with improved blood-device compatibility that minimizes platelet adhesion. In certain embodiments, the air in the micropores of the blood-contacting layer is completely displaced in a hydrating step immediately prior to implantation. The air can be removed by repeatedly soaking the graft in saline and subject to vacuum.

Thus, a method of maintaining patency in a vascular graft comprises:
 pre-hydrating the vascular graft to remove any air in the first microporous biomaterial; and
 implanting the vascular graft by directly connecting the vascular graft to a native blood vessel.

In certain embodiments, maintaining patency refers to less than 20%, less than 10%, or less than 5% reduction of the internal circumference of a cross section of the graft lumen over a period of 12 weeks following implantation.

In certain embodiments, maintaining patency refers to less than 50%, less than 40%, less than 30%, less than 20%, less than 10%, or less than 5% occlusion (by neointimal hyperplasia and/or thrombus) of the cross-sectional area bounded by the inner surface of the graft wall over a period of 12 weeks or following implantation.

In certain embodiments, maintaining patency refers to a PVR of less than 2.0 over a period of 12 weeks following implantation, where the PVR is the peak systolic velocity at the stenosis divided by the peak systolic velocity at midgraft.

The following examples are offered by way of illustration, and not by way of limitation.

EXAMPLES

Example 1

Microporous Silicone Vascular Grafts as AV Shunt

Materials:
 Control grafts (N=4) were ePTFE vascular grafts (from Impra) with regular wall thickness of 6 mm and spiral wrapped ribs for radial reinforcement.
 Test grafts (N=6) were 100% silicone grafts as shown in FIG. 2.
 Some of the control grafts and test grafts were fitted with mid-graft percutaneous ports.
 Sheep were 35-40 kg at time of implant. The animals were heparinized.

Methods

The vascular grafts were implanted in an ovine arteriovenous (AV) shunt model. The control grafts were soaked in heparinized saline prior to implant according to standard clinical practice. The test grafts were prehydrated by immersing in heparinized saline and cycling vacuum until bubbles were no longer visible. The prehydration step ensured that all the air in the pores was displaced.

The grafts were implanted bilaterally in a straight ipsilateral configuration (distal carotid artery to proximal jugular vein). The animals were placed on antiplatelet therapy (salicylic acid and clopidogrel) for the duration of the study.

The grafts were monitored for 8 weeks with noninvasive Doppler ultrasound. At the end of the 8-week period, the animals were sacrificed and the grafts were evaluated with fluoroscopic angiography and Intravascular Ultrasound (IVUS). Tissues were paraffin processed and stained with hematoxylin and eosin.

Results:

The in vivo results demonstrate that silicone grafts according to one embodiment had improved patency, improved flow stability, resistance to tissue encapsulation, resistance to capsule constriction, and improved resistance to bacterial colonization when compared to the control grafts.

Figure 5:
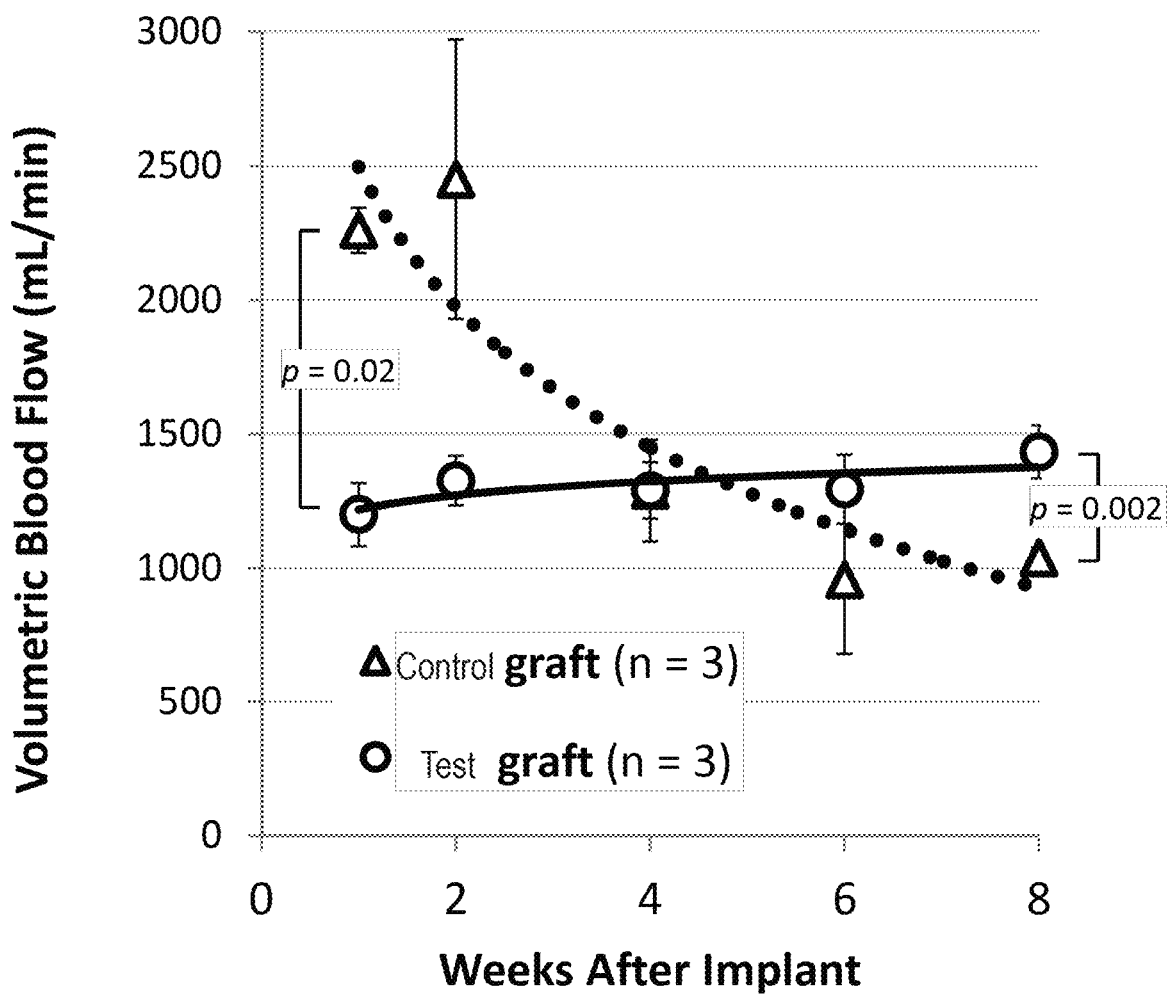
FIG. 5 shows volumetric blood flows in arteriovenous shunts over time in a vascular graft according to an embodiment as compared to a conventional/control vascular graft.

FIG. 5 shows the volumetric blood flow (ml/min) of the control grafts as compared to the silicone grafts. As shown, while the control grafts have downward trending flow, indicating that stenosis was limiting the flow; the silicone test grafts according to the embodiments of the present disclosure have stable flow over the period of 8 weeks following implantation.

FIG. 6A is the angiography image of the control venous graft (100) coupled to a native vein (160). A mid-graft port (170) was also shown. The mid-graft point is T-shaped and is further coupled to an arterial segment graft (172), which is connected to a native artery (174). FIG. 6B is an enlarged view of the control venous graft (100), which shows the narrowing of the blood flow path (arrow). In particular, constrictions are shown along the length of the graft (100a, 100b, 100c and 100d).

FIG. 6C is the angiography image of a silicone test graft (200) coupled to a native vessel (260). A mid-graft port (270) was also shown. The mid-graft point is T-shaped and is further coupled to an arterial segment graft (272), which is connected to a native artery (274). FIG. 6D is an enlarged view of the test graft, which shows that the blood path (arrow) was unaltered and no constrictions were observed.

Figure 7B:
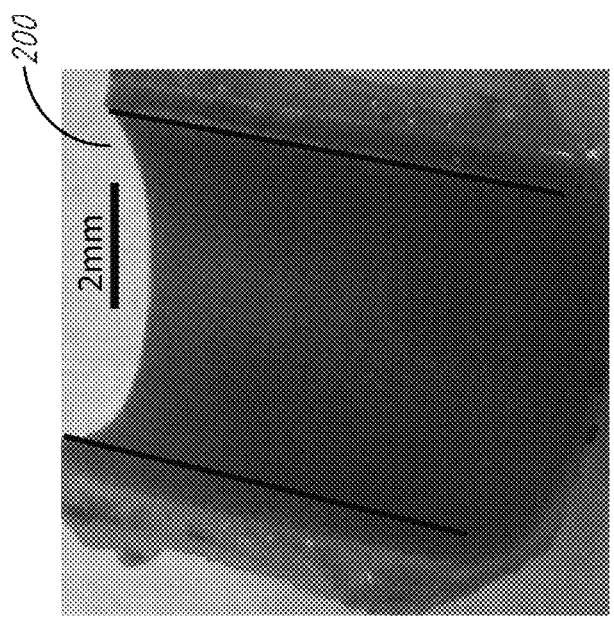
FIGS. 7A and 7B show lengthwise cross sections of explanted vascular grafts of conventional ePTFE with spiral reinforcement and the vascular graft according to an embodiment of the present disclosure, respectively.
Figure 7A:
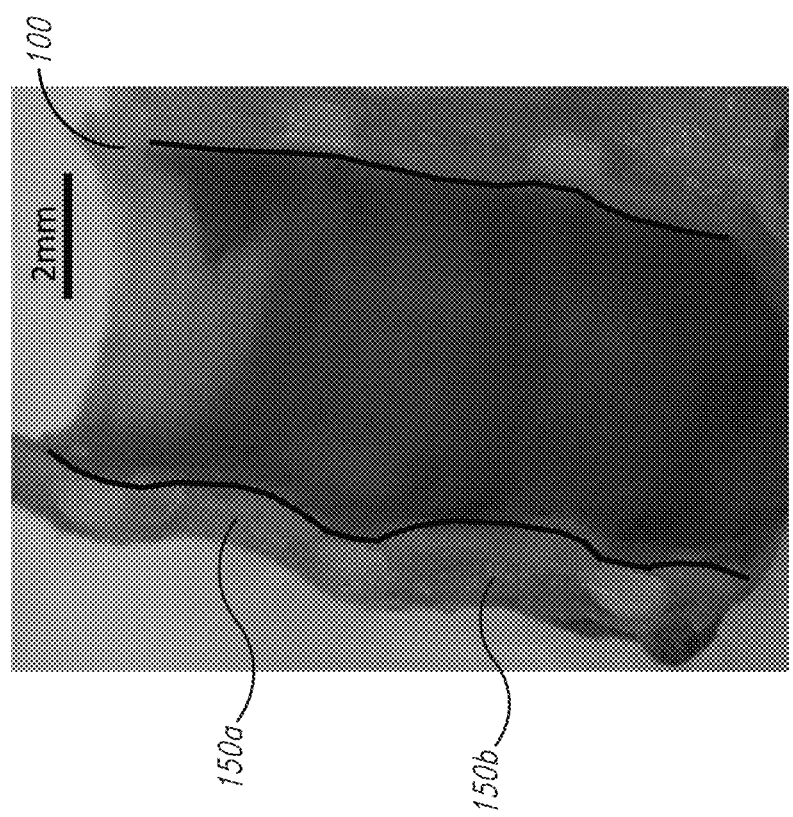

FIGS. 7A and 7B are lengthwise cross sections of explanted vascular grafts of conventional ePTFE (100) and the silicone test graft (200), respectively. FIG. 7A shows that because of the spiral reinforcement, the conventional ePTFE was deformed (constricted) by capsular contraction in the spaces between the reinforcements. Grooves (150a, 150b) in the spaces between reinforcements were formed. This creates an uneven flow surface, leading to increased turbulence and reduced flow stability. In contrast, FIG. 7B shows that the silicone graft (200) was not deformed and thus was capable of maintaining an even flow surface.

Figure 8B:
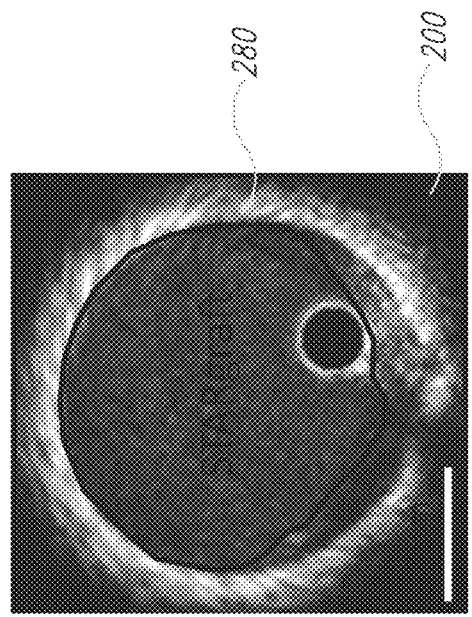
FIGS. 8A and 8B show intravascular ultrasound (IVUS) images of cross sections of a conventional ePTFE graft and a vascular graft according to an embodiment of the present disclosure, respectively.
Figure 8A:
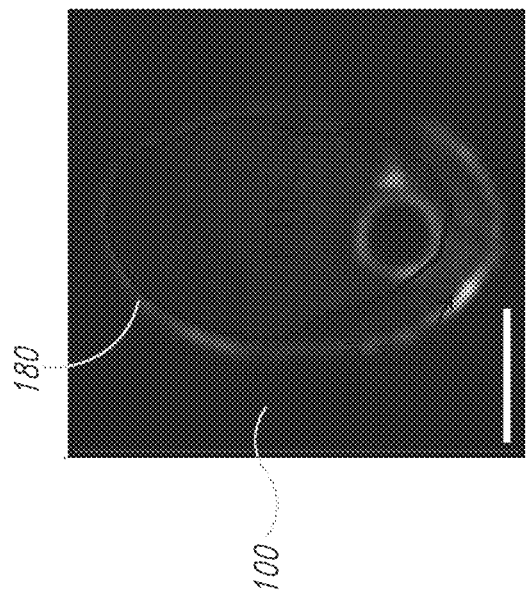

FIG. 8A shows the intravascular ultrasound (IVUS) image of the venous end of the control ePTFE graft (100), which was pinched by capsular contraction, as seen by its constricted profile (180). FIG. 8B shows the IVUS image of the venous end of the silicone test graft (200), which retained its round profile (280) that is significantly larger than that of the control graft.

FIG. 9A and FIG. 9B demonstrate the advantageous tissue response of the tissue encapsulating the graft. FIG. 9A shows that the control graft (100) was encapsulated with thicker, denser and more aligned capsule tissue (190) around the graft. In contrast, FIG. 9B shows that the silicone graft (200) had a much thinner and looser capsule tissue (290) around the graft.

Figure 10:
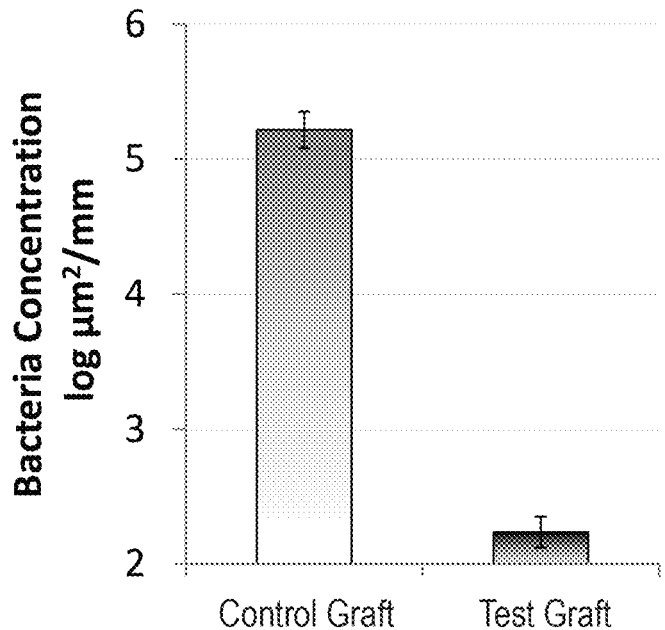
FIG. 10 shows the relative bacterial concentrations within the porous graft walls for a conventional ePTFE graft and a vascular graft according to an embodiment of the present disclosure, respectively.

FIG. 10 further demonstrates, based on color-thresholding of histological images of graft sections, reduced bacterial colonization in the silicone test grafts as compared to the control grafts. In particular, the silicone test graft showed a 1000-fold lower amount of bacteria colonies within the porous structure of the graft wall.

Example 2

Surface-Modified ePTFE Vascular Grafts in AV Shunt Model

Materials:

Control grafts (N=2) were ePTFE grafts (by Vascutek) with regular wall of 6 mm with no radial reinforcement.

Test grafts (N=4) were surface-modified ePTFE grafts as shown in FIGS. 3 and 4. In particular, an ePTFE graft was modified with STAR Biomaterial by dip-coating the outer surface with an adhesive (NuSil MED-2214 silicone), and then adhering a monolayer of granules of sphere-templated microporous silicone. These STAR-treated ePTFE grafts had a surface topography formed by ~300-micron size microporous granules having 35-micron spherical pores, which were interconnected by about 15-micron interpore openings.

Sheep were 65-80 kg at time of implant. The animals were placed on antiplatelet therapy (salicylic acid and clopidogrel) for the duration of the study.

Methods

Vascular grafts were implanted in an ovine arteriovenous (AV) shunt model. As in Example 1, the control grafts were soaked in heparinized saline prior to implant according to standard clinical practice. The test grafts were prehydrated to displace the air in the pore space by immersing the test grafts in heparinized saline and cycling vacuum until bubbles were no longer visible.

The grafts were implanted bilaterally in a straight ipsilateral configuration (distal carotid artery to proximal jugular vein).

The grafts were monitored for 12 weeks with noninvasive Doppler ultrasound. At the end of the 12-week period, the animals were sacrificed and the grafts were evaluated with fluoroscopic angiography and Intravascular Ultrasound (IVUS).

Results:

ePTFE vascular grafts that were surface-modified demonstrated improved patency, reduced stenosis, reduced neointimal hyperplasia, increased capsule tissue compliance, and reversal of the flow-vs-hyperplasia feedback loop from progressively pathologic to self-stabilizing, when compared to the unmodified ePTFE control grafts.

Figure 11:
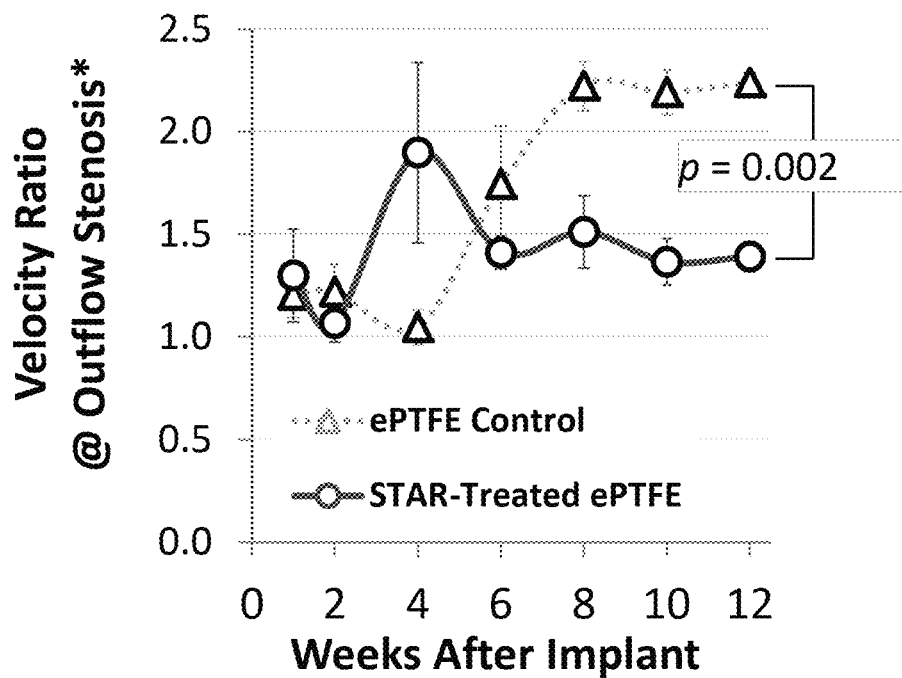
FIG. 11 shows the peak velocity ratio (PVR) in a conventional ePTFE graft as compared to the PVR of a vascular graft according to an embodiment of the present disclosure.

FIG. 11 shows the results of peak velocity ratio (PVR), defined as the peak systolic velocity at the venous anastomosis divided by the peak velocity at midgraft, as measured by Doppler ultrasound over the 12-week period. Because peak systolic velocity ratio (for the venous anastomosis) closely approximates the reciprocal of the lumen area ratio, velocity ratio greater than 2.0 corresponds to a lumen area at the venous anastomosis that is less than 50% of the lumen area at midgraft. As shown, the STAR-treated ePTFE grafts demonstrated much-improved PVR that stabilized after 6 weeks, suggesting a trend of self-stabilizing behavior and reversal of the flow-vs-hyperplasia feedback loop. In contrast, the PVR in the control grafts rose after 4 weeks, indicating a progression of stenosis.

FIG. 12A shows the angiograph images of control grafts, in which stenosis (300a, 300b) in the flow path near the venous anastomosis were clearly visible. By comparison, angiograph images of the STAR-treated grafts show that the flow path for the STAR-treated grafts was relatively smooth, with no obvious stenosis (FIG. 12B).

Figures 13A, 13B:
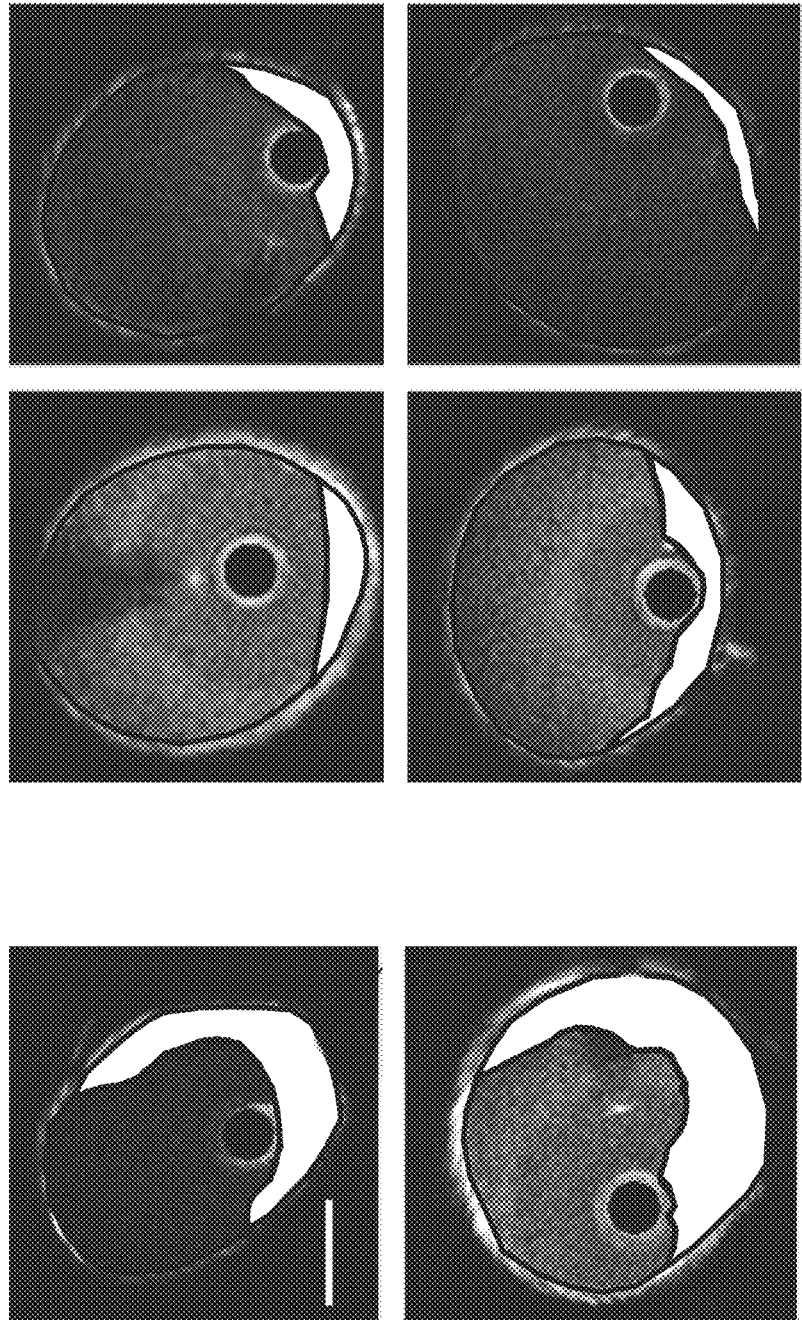
FIGS. 13A and 13B are intravascular ultrasound (IVUS) images of cross sections of conventional ePTFE grafts and vascular grafts according to an embodiment of the present disclosure, respectively.

FIG. 13A shows the intravascular ultrasound (IVUS) images of graft cross sections at the narrowest point along the control grafts. As shown, the control grafts were occluded with neointimal hyperplasia and/or thrombus (white areas). By comparison, the areas of occlusion (white) in the STAR-treated grafts were substantially diminished (FIG. 13B).

Figure 14:
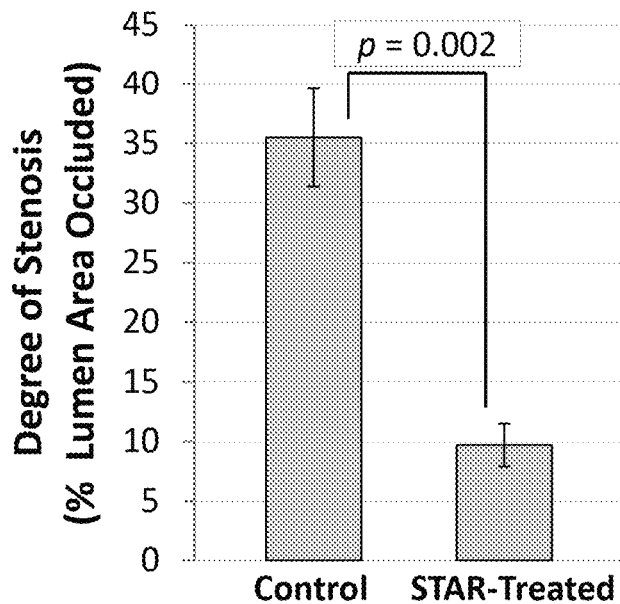
FIG. 14 shows a quantitative comparison of the degrees of stenosis due to neointimal hyperplasia and/or thrombus in conventional ePTFE grafts and vascular grafts according to an embodiment of the present disclosure.

FIG. 14 graphically presents the results of FIG. 13A and FIG. 13B by plotting the average percent lumen area occluded. As shown, for STAR-treated grafts, the percentage lumen area occluded by hyperplasia or thrombus is less than ⅓ of the occlusion observed in the control grafts.

Figure 15:
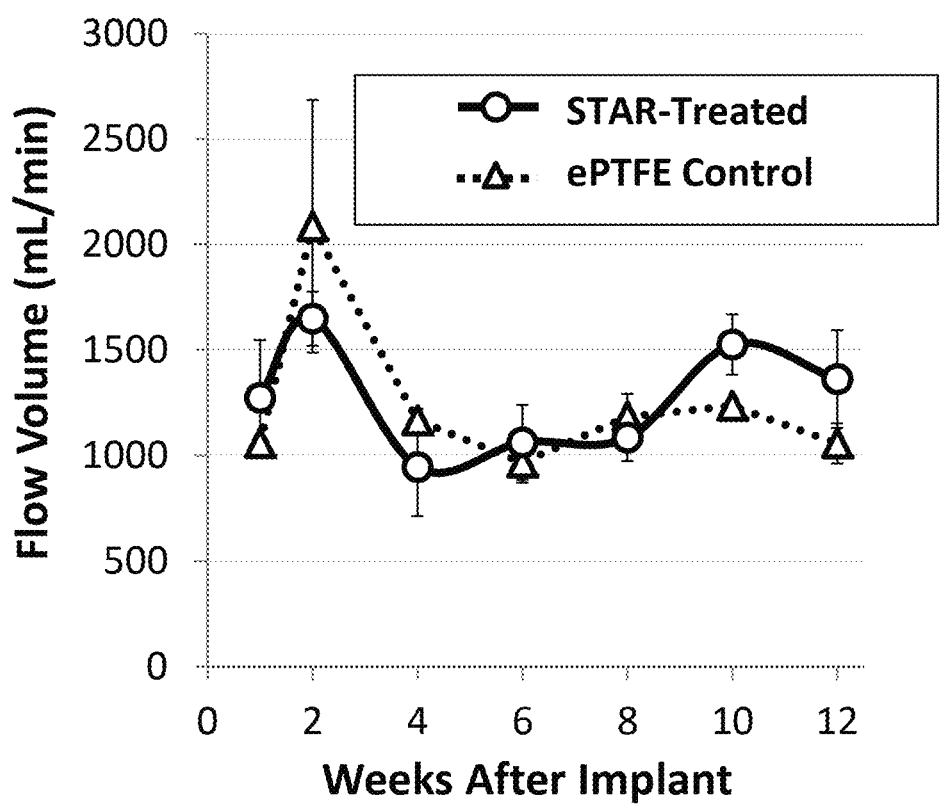
FIG. 15 shows the evolution of the flow volume over time for conventional ePTFE grafts as compared to vascular grafts according to an embodiment of the present disclosure.
Figure 16:
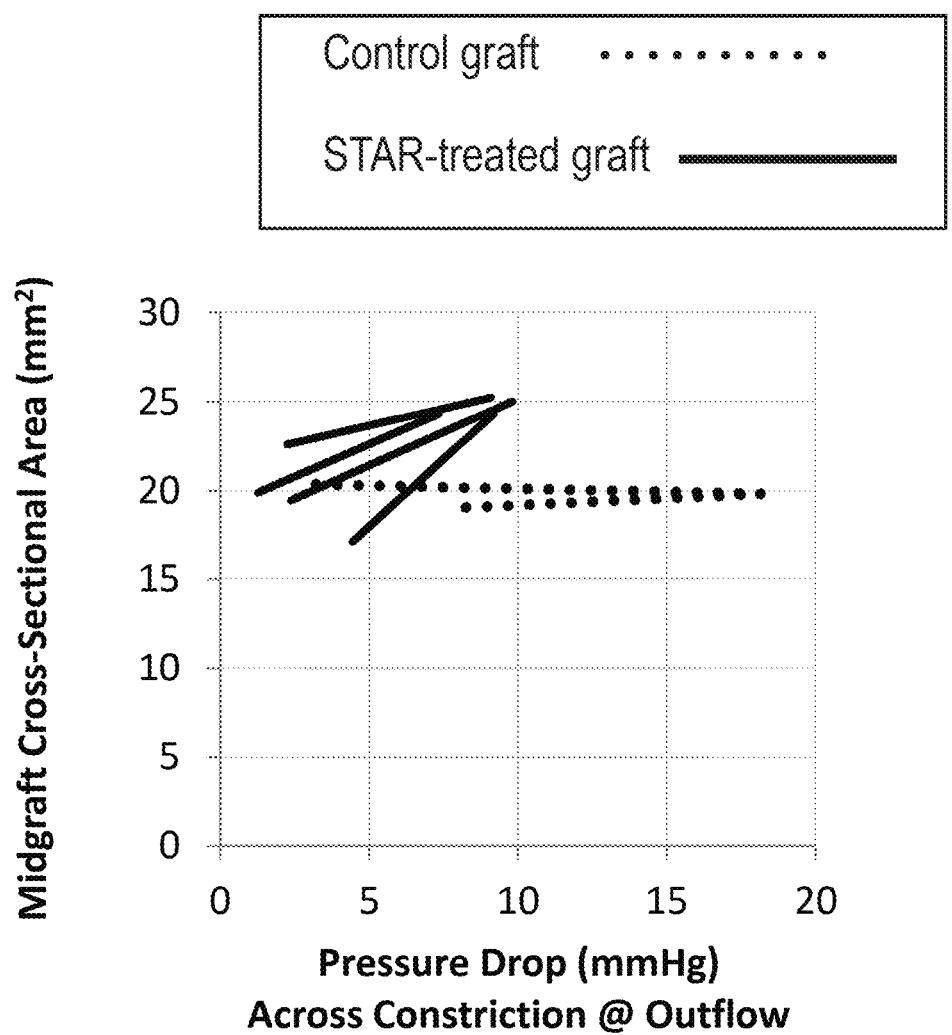
FIG. 16 compares plots of the cross-sectional compliance for conventional ePTFE grafts and vascular grafts according to an embodiment of the present disclosure.

FIG. 15 shows the evolution of the flow for both control and STAR-treated grafts. In the STAR-treated grafts, the average flow volume was nearly 50% greater in the 3rd month of the study than in the 2nd month. The controls did not show this increase. FIG. 16 shows that the STAR-treated grafts had increased cross-sectional compliance. The positive slopes indicate that the mid-graft lumen area expanded proportionally to the Bernoulli's equation-based pressure drop across the venous anastomosis orifice. By comparison, the control grafts had near-zero slopes, indicating the rigidity in the control grafts as a result of perigraft capsular contraction.

Example 3

Surface-Modified ePTFE Vascular Grafts in Arterial Bypass Model

Methods:

Control grafts (N=2) were ePTFE grafts (by Vascutek) with regular wall of 5 mm with no radial reinforcement.

Test grafts (N=2) were surface-modified ePTFE grafts as shown in FIGS. 3 and 4. In particular, an ePTFE graft was modified with STAR Biomaterial by dip-coating the outer surface with an adhesive (NuSil MED-2214 silicone), and then adhering a monolayer of granules of sphere-templated microporous silicone. These STAR-treated ePTFE grafts had a surface topography formed by ~300-micron size microporous granules having 35-micron spherical pores, which are interconnected by about 15-micron interpore openings.

Sheep were 35-40 kg at time of implant. The animals were placed on antiplatelet therapy (salicylic acid and clopidogrel) for the duration of the study.

Methods

The vascular grafts were implanted in a small caliber arterial bypass model. The control grafts were soaked in heparinized saline prior to implant according to standard clinical practice. The test grafts were prehydrated by immersing in heparinized saline and cycling vacuumed until bubbles were no longer visible. The prehydration step ensured that all the air in the pores was displaced.

The grafts were implanted bilaterally in end-to-side configuration in the carotid arteries, then the artery ligated midway between anastomoses.

The grafts were monitored for 8 weeks with noninvasive Doppler ultrasound. At the end of the 8-week period, the animals were sacrificed and the grafts were evaluated with fluoroscopic angiography and Intravascular Ultrasound (IVUS).

Results:

It is further demonstrated in a small caliber arterial bypass model that the surface-treated ePTFE grafts had a reduced constriction from perigraft tissue capsule and improved patency as compared to the untreated ePTFE grafts.

Only 1 of 2 (50%) of the control grafts survived without clotting before reaching the 8-week planned study endpoint, whereas 2 of 2 (100%) of the STAR-treated test grafts remained patent. FIG. 17A and FIG. 17B show longitudinal ultrasound images of a STAR-treated test graft and a control graft at 6 weeks, respectively. The STAR-treated graft has a larger lumen diameter throughout the length with an average diameter of 4.8 mm, as compared to that of the control graft with an average diameter of 4.0 mm. This result suggests that the STAR-treated graft had a lower degree of perigraft capsular contraction due to the surface treatment.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

The invention claimed is:

1. A method for reducing or preventing stenosis caused by neointimal hyperplasia within or near either end of an implanted vascular graft, the method comprising: connecting a vascular graft to one or more native blood vessels to provide the implanted vascular graft in tissue, wherein the vascular graft has a tissue-interface layer having textured microporous surface that reduces constriction from the tissue response to the implanted vascular graft to a degree that reduces neointimal hyperplasia, and wherein the tissue-interface layer comprises interconnected pores that are larger than 20 microns and smaller than 200 microns, and where adjacent pores have inter-pore openings of larger than 5 microns and smaller than 50 microns.

2. The method of claim 1 wherein the vascular graft further comprises a blood-contacting layer defining a lumen of the vascular graft, and a nonporous intermediate layer interposed between the blood-contacting layer and the tissue-interface layer.

3. The method of claim 2, wherein the blood-contacting layer is formed of expanded polytetrafluoroethylene or another fluoropolymer.

4. The method of claim 2, wherein the blood-contacting layer is formed of polyethylene terephthalate fabric.

5. The method of claim 2, wherein the intermediate layer contains fenestrations.

6. The method of claim 1 wherein the textured microporous surface comprises peaks and valleys, wherein the peaks are greater than 200 microns and less than 1000 microns in height.

7. The method of claim 6 wherein the textured microporous surface comprises granules of microporous silicone.

8. The method of claim 1, wherein the tissue-interface layer is formed of silicone.

9. The method of claim 1, wherein the tissue-interface layer is formed of expanded polytetrafluoroethylene or another fluoropolymer.

10. The method of claim 1, wherein the tissue-interface layer is formed of polyurethane.

11. A method for reducing or preventing development of neointimal hyperplasia within or near either end of an implanted vascular graft, the method comprising: connecting a vascular graft to one or more native blood vessels to provide the implanted vascular graft in tissue, wherein the vascular graft has a tissue-interface layer having textured microporous surface that reduces constriction from the tissue response to the implanted vascular graft to a degree that reduces or prevents development of neointimal hyperplasia, and wherein the tissue-interface layer comprises interconnected pores that are larger than 20 microns and smaller than 200 microns, and where adjacent pores have inter-pore openings of larger than 5 microns and smaller than 50 microns.

12. The method of claim 1 wherein the vascular graft further comprises a blood-contacting layer defining a lumen of the vascular graft, and a nonporous intermediate layer interposed between the blood-contacting layer and the tissue-interface layer.

13. The method of claim 12, wherein the blood-contacting layer is formed of expanded polytetrafluoroethylene or another fluoropolymer.

14. The method of claim 12, wherein the blood-contacting layer is formed of polyethylene terephthalate fabric.

15. The method of claim 12, wherein the intermediate layer contains fenestrations.

16. The method of claim 11 wherein the textured microporous surface comprises peaks and valleys, wherein the peaks are greater than 200 microns and less than 1000 microns in height.

17. The method of claim 16 wherein the textured microporous surface comprises granules of microporous silicone.

18. The method of claim 11, wherein the tissue-interface layer is formed of silicone.

19. The method of claim 11, wherein the tissue-interface layer is formed of expanded polytetrafluoroethylene or another fluoropolymer.

20. The method of claim 11, wherein the tissue-interface layer is formed of polyurethane.

* * * * *